United States Patent [19]

Vecchio

[11] 4,439,419
[45] Mar. 27, 1984

[54] METHOD OF TREATING GASTRIC HYPERACIDITY IN HUMANS EMPLOYING A COPOLYMER OF POLYETHYLENEPOLYAMINE AND A BIFUNCTIONAL SUBSTANCE AS EPICHLORHYDRIN

[75] Inventor: Thomas J. Vecchio, Kalamazoo, Mich.

[73] Assignee: The Upjohn Company, Kalamazoo, Mich.

[21] Appl. No.: 247,487

[22] Filed: Mar. 25, 1981

Related U.S. Application Data

[63] Continuation of Ser. No. 122,873, Feb. 20, 1980, abandoned.

[51] Int. Cl.³ .............................................. A61K 31/74
[52] U.S. Cl. ...................................................... 424/78
[58] Field of Search .................................... 424/78, 79

[56] References Cited

U.S. PATENT DOCUMENTS

| | | | |
|---|---|---|---|
| 3,224,940 | 12/1965 | Ainsworth et al. | 424/78 |
| 3,332,841 | 7/1967 | Ainsworth et al. | 424/78 |
| 3,692,895 | 9/1972 | Nelson et al. | 424/78 |
| 3,803,237 | 4/1974 | Lednicer et al. | 424/78 |
| 4,172,120 | 10/1979 | Todd et al. | 424/79 |
| 4,191,744 | 3/1980 | Bogentoft | 424/78 |
| 4,252,790 | 2/1981 | Higuchi | 424/79 |

OTHER PUBLICATIONS

The New England Journal of Medicine, vol. 288, Feb. 8, 1973, No. 6, 273-276.

Primary Examiner—Frederick E. Waddell
Attorney, Agent, or Firm—William G. Jameson; John J. Killinger

[57] ABSTRACT

This invention relates to the new use of a known polymeric material for the neutralizing of gastric acidity and treating hyperacidity in humans having an excess of gastric acidity and the treatment of ulcers. The polymeric material is a copolymer of polyethylenepolyamine and a bifunctional substance. Oral pharmaceutical dosage forms and doses are shown.

4 Claims, No Drawings

METHOD OF TREATING GASTRIC HYPERACIDITY IN HUMANS EMPLOYING A COPOLYMER OF POLYETHYLENEPOLYAMINE AND A BIFUNCTIONAL SUBSTANCE AS EPICHLORHYDRIN

This is a continuation of application Ser. No. 122,873, filed Feb. 20, 1980, now abandoned.

BRIEF SUMMARY OF THE INVENTION

This invention relates to the new use of a known polymeric material for the neutralizing of gastric acidity and treating hyperacidity in humans having an excess of gastric acidity and the treatment of ulcers. The polymeric material is a copolymer of polyethylenepolyamine and a bifunctional substance and one such polymeric material is known as colestipol hydrochloride and used in reducing serum cholesterol in humans.

DETAILED DESCRIPTION

In accordance with the manner and process of using the present invention, a sufficient amount of the copolymer agent is orally administered to affected mammals, animals and birds to provide beneficial effects in lowering gastric acidity in said mammals, for example, humans; animals such as dogs; and birds such as chickens. The gastric acidity lowering agent can be administered as such, or after suitably compounding into unit dosage forms with a nontoxic, compatible, edible oral carrier, e.g., an aqueous vehicle. The polyethylenepolyamines used in preparing the copolymers are those of the ethylenediamine series containing from 2 to about 10 ethylene units, the molecular weight ranging from about 103 to an average molecular weight of about 450. A lower member of the series, diethylenetriamine, molecular weight about 103, is usually available commercially in both pure and commercial grades. Triethylenetetramine, tetraethylenepentamine, pentaethylenehexamine, and the higher homologs are usually available as commercial grades containing aliphatic and also some cyclic polyethylenepolyamines. See, for example, the disclosure of mixed residues containing up to about 10 alkylene groups in U.S. Pat. No. 3,152,188. Commercially available polyethylenepolyamines are derived, for example, from the reaction of ethylene dichloride and ammonia or the controlled polymerization of ethyleneimine. Jones, et al. J. Org. Chem. 9:125-147 (1944) describe the polymerization of ethyleneimine by catalysts such as acids, boron trifluoride and ammonia. Polyethylenepolyamines therein described include diethylenetriamine, triethylenetetramine, tetraethylenepentamine, heptaethyleneoctamine, nonaethylenedecamine, as well as higher molecular weight polymers with lesser amounts of amino nitrogen. Gause, et al., J. Amer. Chem. Soc. 73:5457 (Nov.) 1951 describe purification of tetraethylenepentamine on an ion exchange column. Hutchinson, et al., J. Amer. Chem. Society 67:1966 (Nov.) 1945 describe formation of diethylenetriamine, triethylenetetramine, tetraethylenepentamine and similar compounds of higher molecular weights, the latter being found in an "amine residue" after removal of the lower members by distillation. Ionescu and Anghelescu, Chem. Abstracts 64:1357 (1966) describe gas chromatographic analysis of polyethylenepolyamines which indicates that ethylenediamine, diethylenetriamine, triethylenetetramine, tetraethylenepentamine and pentaethylenehexamine are usually present in mixtures. Polyalkylenepolyamines are also described and used in U.S. Pat. Nos. 2,644,760 and 3,152,188. Those described in U.S. Pat. No. 2,644,760 are polyamines of the ethylenediamine series and include, for example, tetraethylenepentamine, triethylenetetramine, diethylenetriamine, pentaethylenehexamine, and the like. Those described in U.S. Pat. No. 3,152,188 include diethylenetriamine, triethylenetetramine and tetraethylenepentamine in pure form or as mixtures, and higher polyalkylenepolyamine homologs which are usually marketed as mixed residues containing up to approximately 10 alkylene units.

Polyethyleneimine polymers are described and used in U.S. Pat. Nos. 3,308,020 and 3,332,841. Those in the former have an average molecular weight of about 30,000 and those in U.S. Pat. No. 3,332,841 have an average molecular weight of from about 800 to about 100,000. However, in the present invention, a molecular weight range of from about 103 (diethylenetriamine) to an average molecular weight of about 450 includes those polyethylenepolyamines useful for the preparation of crosslinked copolymers administered orally. The aforesaid polyethylenepolyamines are available as marketed products of various suppliers such as Dow Chemical Company, Industrial Chemical & Dye Company, Union Carbide, Aldrich Chemical Co., and Eastman Kodak. Typically supplied commercial tetraethylenepentamine (Union Carbide) has nominal values as follows: apparent specific gravity, 20/20° C., 0.9980; boiling point 760 mm., 340° C. (decomposes); completely soluble in water, flash point, ASTM method D92, Cleveland Open Cup, 365° F.

In order to prepare the copolymers for the inventive process, such polyethylenepolyamines are copolymerized and cross-linked with bifunctional compounds having epoxy groups and/or halogen atoms; for example, epichlorohydrin, glycerol-1,3-dichlorohydrin, 1,2:3,4-diepoxybutane, bis-epoxypropyl ether, ethylene glycol bis-epoxypropyl ether and 1,4-butanediol bis-epoxypropyl ether according to known methods; for example, those of British Patent No. 628,821; U.S. Pat. No. 3,002,823; Peterson and Sober, J. Am. Chem. Soc. 78:751-755 (1956), and McKernan and Ricketts, Chemistry and Industry, Nov. 21, (1959) pgs. 1490-1491. Illustratively, with epichlorohydrin as cross-linking agent the copolymer contains cross-links represented by $-CH_2CHOHCH_2-$; with 1,2:3,4-diepoxybutane by $-CH_2CHOHCHOHCH_2-$; with bis-epoxypropyl ether by $-CH_2CHOHCH_2OCH_2CHOHCH_2-$. Similarly, with ethylene glycol bis-epoxypropyl ether the copolymer contains cross-links represented by $-CH_2CHOHCH_2OCH_2CH_2OCH_2CHOHCH_2-$, and in the case of 1,4-butanediol bis-epoxypropyl ether by $-CH_2CHOHCH_2O(CH_2)_4OCH_2CHOHCH_2-$. Hence, these copolymer cross-linked products contain a residue of an aliphatic radical having three to ten carbon atoms inclusive. The content of cross-linking moiety expressed as % by weight of the copolymer is at least 10%, preferably at least 14%, and reaches in some cases 47% or higher. Both the partial acid addition salts and free base forms of the cross-linked copolymer are operable in the present compositions and processes. Illustratively, a pharmaceutically acceptable hydrochloric acid addition salt form is prepared by controlling the amounts of the polyethylenepolyamine and bifunctional reactant and using calculated amounts of base, e.g., sodium hydroxide, in adjusting the reaction mixture, for example, 20 moles of tetraethylenepentamine, 50 moles of epichlorohydrin and 50 moles of sodium hydroxide provide a cross-linked copolymer in the form of a partial hydrochloride. Alternately, an acid addition salt is prepared from an aqueous solution, dispersion or suspension of a free base copolymer by adjustment with the desired acid, such as phosphoric, citric, sulfuric, hydrochloric and the like. For example, 650 gm of free base copolymer of tetraethylenepentamine and epichlorohydrin and 75 gm of sulfuric acid provide a copolymer partial sulfate. Illustratively, free base forms are usually prepared by adding excess alkali, e.g., sodium hydroxide, to the reaction mixture of a particular amine and bifunctional reactant, thus obtaining an alkaline aqueous dispersion or suspension of the free base. Washing with distilled or deionized water until the washings are free of the acid ion and free of alkali provides the base which is dried at about 80° C. and milled to a uniform granular solid.

A preferred method for preparing the polymer for medical use is disclosed in U.S. Pat. No. 3,803,237, issued Apr. 9, 1974, and is known as the "bead process".

The polymer suitably prepared as required or desired with an edible oral carrier in an oral dosage form is administered in varying amounts depending upon the weight of the mammals and birds under treatment. In the case of affected human subjects having gastric hyperacidity, the total dosage ranges from about 2 gm to about 100 gm, preferably from about 10 gm to about 20 gm. The preferred regimen of the oral administration is three to four times daily. The individual dosage amount ranges from about 0.5 gm to about 25 gm, usually four times a day, preferably about 1.0 gm to about 5.0 gm dosage amount four times a day. The active ingredient is suitably reduced to a particle size of no more than about 50 microns. Oral administration of the polymers provides a method of neutralizing gastric acids and combatting hyperactivity and treating gastric ulcers which is free of the unsatisfactory and unacceptable taste and/or odor which usually accompany methods utilizing, for example, excessively oily vehicles or quaternary ammonium ion exchangers based on polystyrenes with divinylbenzene moieties. In addition to treating gastric ulcers, the following conditions can be treated: peptic ulcers, duodenal ulcers, esophageal ulcers, esophagitis, gastritis, duodenitis and functional hyperacidity.

The term "edible oral carrier" means the diluents, excipients, aqueous vehicles, oily vehicles, binders, disintegrators, and lubricants, such as calcium carbonate, lactose, calcium phosphate, water, fruit juice, vegetable juice, safflower oil, talc, starch, magnesium stearate, and the like, used by those skilled in the art in preparing oral dosage forms and products such as hard and soft capsules, gels, magmas, powders, dispersions, solutions, emulsions, suspensions, granules, and coated and uncoated tablets.

PREPARATION 1

To a warm solution of 3.78 kg (20 moles) of tetraethylenepentamine in 40 liters of water is added 4.6 kg (50 moles) of epichlorohydrin. After the exothermic reaction subsides (about one hour), 4 kg of 50% aqueous sodium hydroxide solution (50 moles) is added. The resulting gel is transferred to flat trays and air-dried at 80° C. The dry solid is suspended in water, the suspension is filtered, and the filter case washed with water. The cake is air-dried at 80° C. to 6.8 kg of copolymer which is then milled to produce a uniform granular solid suitable for use in formulation.

PREPARATION 2

Copolymer Free Base 700 gm of granular solid prepared as in Preparation 1, approximately 1 in 5 nitrogen atoms protonated as the hydrochloride, is suspended in 4000 ml water containing 95 gm of sodium hydroxide and the whole is uniformly mixed. After about 60 minutes the suspension is filtered and the filter cake is washed with deionized water until the wash water is found free of chloride ion by silver nitrate test and found free of sodium hydroxide by pH test. The filter cake is then dried at about 80° C., yielding 600 gm of polymer free base which is milled to produce a uniform granular solid suited for use in formulating orally administered pharmaceutical preparations.

PREPARATION 3

This procedure shows a typical scale of operation. Multiples or fractions of this operating scale may also be employed.

A mixture of 183 l. of deionized water, 0.133 kg. Richonate 60B solids (added as aqueous solution), 100 kg. diethylenetriamine, and 960 l. toluene is stirred and heated almost to reflux temperature (78°–84° C.). Epichlorohydrin, 173 kg. is then added gradually while refluxing the solution, and refluxing is continued for approximately two hours after the epichlorohydrin addition is complete. 109 kg. of 50% sodium hydroxide solution is added. The mixture is removed from the reaction, filtered and the copolymer is collected and dried. The product is washed several times with a total of at least ten times its weight of deionized water. It is then filtered and dried. Drying is accomplished either in a vacuum tumbler dryer with 80°–90° C. jacket temperature or in a continuous dryer in which moisture is removed by a stream of heated air. When dried by the latter method, the polymer can be brought to final moisture specification in a vacuum tumbler dryer. After drying it may be necessary to machanically break up clumps of agglomerated beads of polymer. The copolymer hydrochloride prepared as described in the above example gives the following typical analytical values, it being understood that variations from batch to batch, within the ranges shown, are to be expected:

Elemental analyses—C, 50.3–52.7%; H, 9.0–11.0%; Cl, 6.5–9.0%; N, 17.0–19.0%.

Ash. not to exceed 0.5%.

Moisture: not to exceed 1.0%. Particle diameter: 0.001–0.03 inch.

Exchange capacity: 8.0–11.0 meq./gm.

Binding capacity: 1.1–1.6 meq./gm.

PREPARATION 4

Into a 1,000 gallon, jacketed, glass-lined reactor equipped with baffles and a two-speed (67 and 135 r.p.m.) reserved impeller is introduced 200 g. of Richonate 60B (a 60% aqueous slurry of sodium salts of alkylbenzenesulfonic acids) and 364 l. of deionized water, followed by 90.5 kg. of tetraethylenepentamine rinsed in with 5 gallons of toluene. The solution is stirred at the low speed and then 500 gallons of toluene are added to form a dispersion. To the stirred dispersion is added 109 kg. of epichlorohydrin, rinsed in with 5 gallons of toluene, and the resulting mixture is heated at reflux for two hours. The reaction mixture is cooled to about 20° C. and then treated with 58.5 kg. of a filtered 50% aqueous solution of sodium hydroxide. The mixture is removed from the reactor and filtered, and the copolymer is collected and dried by treating it first with hot (75°–80° C.) filtered nitrogen and then with an 80° C. air stream. The resulting crude product is returned to the reactor, washed extensively with filtered deionized water (at the low speed), dried with an 80° C. air stream and blended until homogeneous to give about 155 kg. of a dry tetraethylenepentamine-epichlorohydrin copolymer particle hydrochloride, particle diameter 0.002–0.02 inch.

The copolymer hydrochloride prepared as described in the above example gives the following typical analytical values, it being understood that variations from batch to batch, within the ranges shown, are to be expected:

Elemental analyses—C, 50.3–52.7%; H, 9.0–11.0%; Cl, 7.3–9.3%; N, 17.0–19.0%.

Ash: not to exceed 0.5%.

Moisture: not to exceed 1.0%. Particle diameter: 0.001–0.03 inch.

EXAMPLE 1

Capsule

One thousand two-piece hard gelatin capsules for oral use, each containing 500 mg of tetraethylenepentamineepichlorohydrin copolymer are prepared from the following ingredients:

| | |
|---|---|
| Tetraethylenepentamine-epichlorohydrin copolymer free base | 500 gm |
| Talc, U.S.P. | 50 gm |
| Magnesium Stearate, U.S.P. | 2 gm |

The finely powdered ingredients are mixed thoroughly, then filled into hard gelatin capsules of appropriate size.

Two capsules are taken four times a day to lower gastric acidity in hyperacidic patients.

EXAMPLE 2

Powder Packets

Ten thousand powder packets, each containing 5.0 gm of a diethylenetriamine-epichlorohydrin copolymer partial hydrochloride are prepared from the following:

| | |
|---|---|
| Diethylenetriamine-epichlorohydrin copolymer particle hydrochloride | 50,000 gm |

One or two packets emptied and stirred into water, fruit or vegetable juices, skimmed milk, or mixed with cereal, applesauce or other food, is given four times daily in the relief of hyperacidity associated with gastric ulcers.

EXAMPLE 3

Aqueous Dispersion

An aqueous oral dispersion containing in each tablespoon (15 ml) 1,000 mg of a polyethylenepolyamine-epichlorohydrin copolymer is prepared from the following materials:

| | |
|---|---|
| Polyethylenepolyamine-epichlorohydrin copolymer free base | 1,000 gm |
| Pectin, N.F. | 100 gm |
| Deionized water, q.s. | 15,000 ml |

One tablespoon (15 ml) is given three times a day to lower gastric acidity in ulcer patients.

EXAMPLE 6

Powder Packets

Five thousand powder packets, each containing 25 gm of polyethylenepolyamine-epichlorohydrin copolymer are prepared from 125,000 gm of the polymer.

One packet emptied and dispersed into an aqueous vehicle such as water, fruit or vegetable juice, skimmed milk, or the like is taken four times daily to reduce gastric acidity in ulcer patients.

I claim:

1. A method of reducing gastric acidity in the absence of bile acid reflux in an affected mammal or human which consists essentially of orally administering to said mammal or human an effective amount for reducing gastric acidity in said animal or human of the free base or partial acid addition salt form of a cross-linked copolymerization product of (a) a polyethylenepolyamine containing from about 2 to about 10 ethylene units and (b) a member selected from the group consisting of epichlorohydrin, glycerol-1,3-dichlorohydrin, 1,2:3,4-diepoxybutane, bis-epoxypropyl ether, ethylene glycol bis-eopxypropyl ether and 1,4-butanediol bis-epoxypropyl ether.

2. The method of claim 1 wherein the polyethylenepolyamine is tetraethylenepentamine and the member is epichlorohydrin.

3. The method of claim 1 wherein the amount administered is from about 1.0 to about 100 gm daily.

4. The method of claim 1 wherein the polyethylenepolyamine is diethylenetriamine and the member is epichlorohydrin.

* * * * *

UNITED STATES PATENT OFFICE
CERTIFICATE OF CORRECTION

Patent No. 4,439,419  Dated March 27, 1984

Inventor(s) Thomas J. Vecchio

It is certified that error appears in the above-identified patent and that said Letters Patent are hereby corrected as shown below:

Front Page [54] in 5th line of Title: "Substance as Epichlorhydrin" should read -- Substance such as Epichlorhydrin --.
Column 1, line 5: "Substance as" should read -- Substance such as --.
Column 3, line 26: "total dosage" should read -- total daily dosage --.
Column 3, line 36: "hyperactivity" should read -- hyperacidity --.

Signed and Sealed this

Thirteenth Day of November 1984

[SEAL]

Attest:

GERALD J. MOSSINGHOFF

Attesting Officer    Commissioner of Patents and Trademarks